(12) United States Patent
Houser et al.

(10) Patent No.: US 9,271,751 B2
(45) Date of Patent: Mar. 1, 2016

(54) ULTRASONIC SURGICAL SYSTEM

(75) Inventors: Kevin L. Houser, Springboro, OH (US);
Foster B. Stulen, Mason, OH (US);
Stephanie J. Muir, Loveland, OH (US)

(73) Assignee: Ethicon Endo-Surgery, LLC,
Guaynabo, PR (US)

( * ) Notice: Subject to any disclaimer, the term of this patent is extended or adjusted under 35 U.S.C. 154(b) by 1333 days.

(21) Appl. No.: 11/807,474

(22) Filed: May 29, 2007

(65) Prior Publication Data

US 2008/0300611 A1      Dec. 4, 2008

(51) Int. Cl.
*A61B 17/32*      (2006.01)
*A61B 17/3203*    (2006.01)

(52) U.S. Cl.
CPC ..... *A61B 17/320068* (2013.01); *A61B 17/3203* (2013.01); *A61B 2017/320044* (2013.01); *A61B 2017/320072* (2013.01); *A61B 2017/320084* (2013.01)

(58) Field of Classification Search
CPC .................. A61B 17/00234; A61B 17/320068
USPC ................................. 606/79, 83–85, 167–171
See application file for complete search history.

(56) References Cited

U.S. PATENT DOCUMENTS

| | | | |
|---|---|---|---|
| 4,700,716 A | 10/1987 | Kasevich et al. | |
| 4,827,911 A | 5/1989 | Broadwin et al. | |
| 4,832,683 A | 5/1989 | Idemoto et al. | |
| 5,058,570 A * | 10/1991 | Idemoto et al. | 601/4 |
| 5,569,161 A | 10/1996 | Ebling et al. | |
| 6,090,120 A | 7/2000 | Wright et al. | |
| 6,254,623 B1 | 7/2001 | Haibel, Jr. et al. | |
| 6,893,434 B2 | 5/2005 | Fenton et al. | |
| 6,929,632 B2 * | 8/2005 | Nita et al. | 604/508 |
| 6,976,969 B2 | 12/2005 | Messerly | |
| 7,122,017 B2 | 10/2006 | Moutafis et al. | |
| 7,135,029 B2 | 11/2006 | Makin et al. | |
| 2003/0176791 A1 | 9/2003 | Rabiner et al. | |
| 2004/0176717 A1 | 9/2004 | Honda et al. | |
| 2004/0204728 A1 | 10/2004 | Haefner | |
| 2005/0234484 A1 | 10/2005 | Houser et al. | |
| 2005/0267502 A1 * | 12/2005 | Hochman | 606/167 |
| 2006/0025709 A1 | 2/2006 | Whitmore et al. | |
| 2006/0079879 A1 | 4/2006 | Faller et al. | |

(Continued)

FOREIGN PATENT DOCUMENTS

| JP | 2004267462 | 9/2004 |
|---|---|---|
| JP | 2006142112 | 6/2006 |

(Continued)

OTHER PUBLICATIONS

International Search Report and Written Opinion of the International Search Authority, Sep. 29, 2008, PCT/US2008/63485, pp. 4, U.S. Patent and Trademark Office.

(Continued)

*Primary Examiner* — David Bates
*Assistant Examiner* — Olivia C Chang

(57) ABSTRACT

An ultrasonic surgical system includes an ultrasonic transmission member having a proximal end and a distal end. An ultrasonically actuated end-effector is attached at the distal end of the transmission member. A pressurized fluid delivery system includes a fluid nozzle in communication with at least one fluid source. The fluid nozzle is arranged and configured to deliver pressurized fluid to soft tissue at a rate to move the soft tissue away from the end-effector during use.

20 Claims, 13 Drawing Sheets

(56) References Cited

U.S. PATENT DOCUMENTS

| | | | |
|---|---|---|---|
| 2006/0211989 | A1 | 9/2006 | Rinehart et al. |
| 2006/0235306 | A1 | 10/2006 | Cotter et al. |
| 2006/0265035 | A1 | 11/2006 | Yachi et al. |
| 2006/0269901 | A1 | 11/2006 | Rosenblood et al. |
| 2007/0010861 | A1 | 1/2007 | Anderson et al. |
| 2007/0049923 | A1 | 3/2007 | Jahns |
| 2008/0234708 | A1* | 9/2008 | Houser et al. ............ 606/169 |

FOREIGN PATENT DOCUMENTS

| | | |
|---|---|---|
| JP | 2006341066 | 12/2006 |
| JP | 2011253451 | 12/2011 |
| WO | 2004/037095 | 5/2004 |
| WO | WO 2007/013076 | 2/2007 |

OTHER PUBLICATIONS

EP, Search Report, European Application No. 08755354.1 (May 27, 2011).

PCT, International Preliminary Report on Patentability, International Application No. PCT/US2008/063485 (Dec. 1, 2009).

Japanese Patent Office; Notification of Reasons for Refusal; Patent Application JP 2010-210404; Mailing No. 803926; Mailing Date, Nov. 27, 2012.

PCT Application Japanese Translation Publication 2009-502304.

Japanese Office Action, Application No. 2010-510404, dated Nov. 27, 2012.

AU Application No. 2008260378, Patent Examination Report No. 2 issued Oct. 8, 2013.

\* cited by examiner

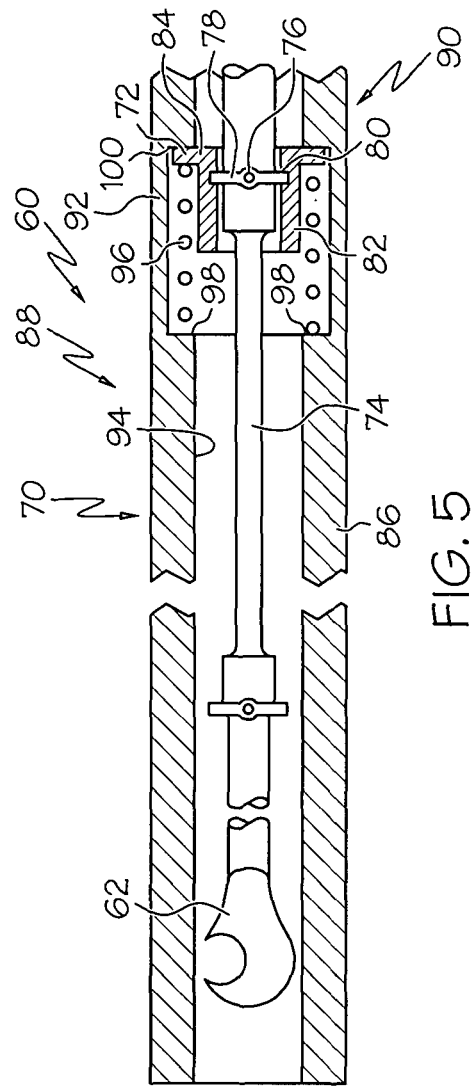
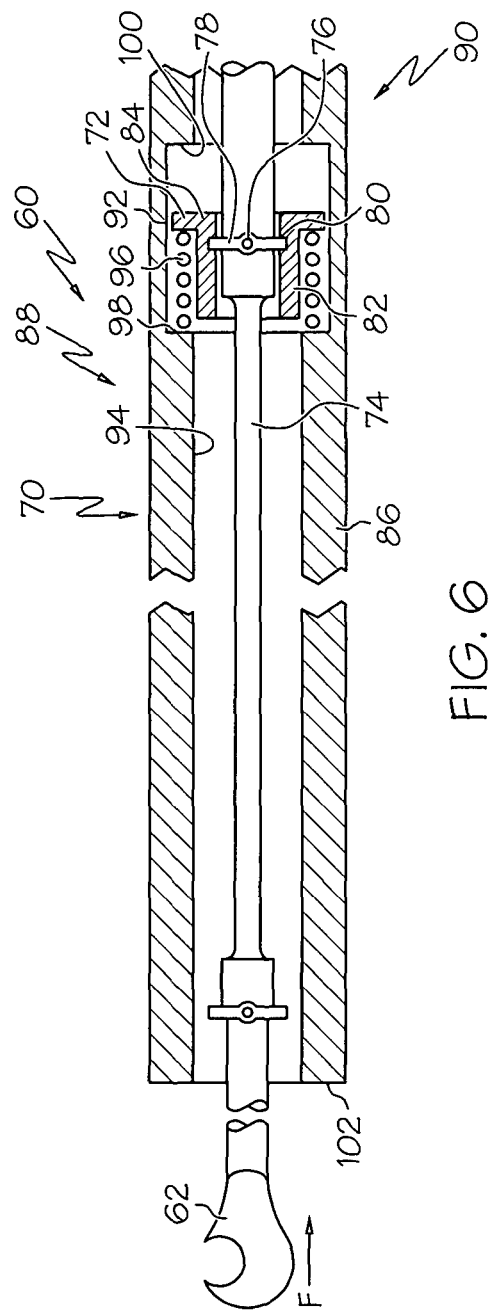

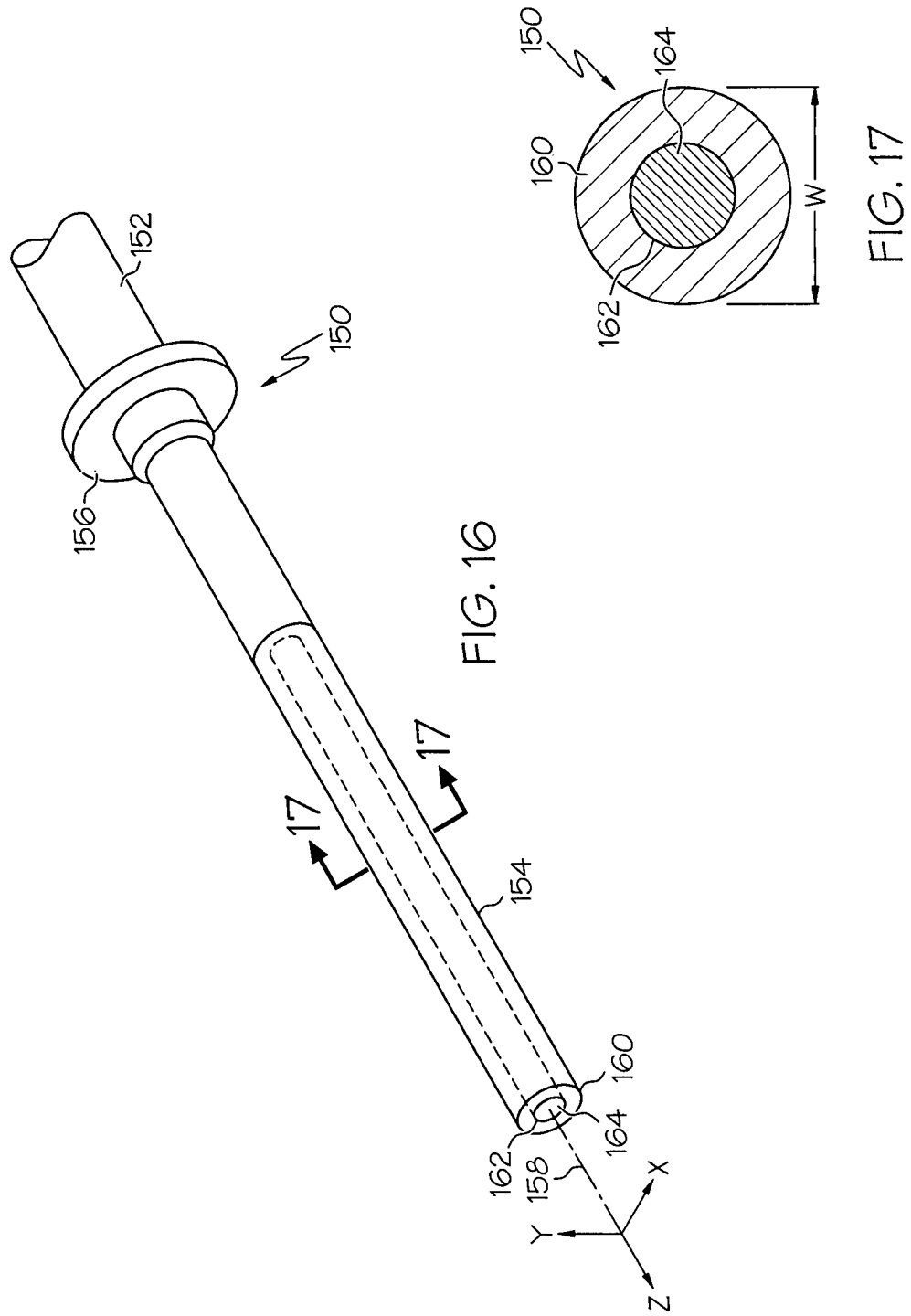

ULTRASONIC SURGICAL SYSTEM

TECHNICAL FIELD

The present application relates generally to surgical systems, and more particularly to ultrasonic surgical systems.

BACKGROUND

Surgeons use ultrasonic instruments in surgery to cut and coagulate tissue. Piezoelectric elements are electrically excited at a resonant frequency of an ultrasonic instrument to create vibrations that are transmitted through a resonator and amplified to produce a mechanical, standing wave vibration of the same frequency. An ultrasonic transmission assembly of the instrument has an elongated, transmission waveguide that transmits this vibration to an end effector (e.g., cutting blade) on the distal tip of the instrument. The end effector may vibrate primarily in the longitudinal direction to generate localized heat within adjacent tissue, although some instruments have been designed specifically so that the end effector vibrates primarily in either of the transverse (perpendicular to the longitudinal axis) or torsional (about the longitudinal axis) directions to treat tissue.

The distal tip of the end effector corresponds to a vibratory anti-nodal point. The proximal end of the end effector typically attaches to the waveguide slightly distal to the most distal, vibratory nodal point of the ultrasonic transmission assembly. This arrangement allows tuning of the instrument to a preferred resonant frequency when the end effector is not loaded with tissue. In some embodiments, the length of the end effector is slightly less than one-quarter of the acoustic wavelength that propagates through the end effector material when excited by an ultrasonic energy input of a particular frequency.

Ultrasonic surgical end effectors formed from different materials may exhibit significantly different acoustical and mechanical characteristics. These characteristics may be associated with material properties such as ultrasonic propagation wavelength, conductive heat transfer, mechanical fatigue strength and acoustic transmission efficiency. For example, an end effector formed from a material such as a ceramic having a relatively high ratio of elastic modulus to density may have a longer ultrasonic propagation wavelength than that of an end effector formed from a material such as a metal having a relatively low ratio.

End effectors of some current ultrasonic surgical instruments are made of a Ti-6Al-4V titanium alloy. The ultrasonic propagation wavelength of the titanium alloy is about 87 mm when operated at an ultrasonic frequency of 55.5 kHz, so that the length of the end effector is about 22 mm. For certain surgical applications the surgeon may prefer a slightly longer end effector than what is currently available.

The acoustic wavelength in a material is equal to the speed of sound in the material divided by the frequency (cycles/sec.) of the ultrasonic energy input. Therefore, one way to provide instruments with longer end effectors is to decrease the frequency of the ultrasonic energy input. For example, reducing the frequency from approximately 55.5 kHz to approximately 27.8 kHz increases the characteristic wavelength in a titanium alloy to approximately 174 mm. However, there is a practical lower limit to excitation frequency. An end effector vibrating below 20 kHz may create a painfully audible sound to humans and obviously would not be desirable in a surgical operating room.

Another way to provide instruments with longer end effectors is to select end effector materials in which sound travels faster. The speed of sound in a material is a function of material density and modulus of elasticity. Basically, materials having a high elastic modulus to density ratio propagate ultrasonic energy faster than materials having a relatively low ratio. Certain ceramic materials, including alumina ($Al_2O_3$), exhibit characteristic wavelengths that are approximately twice as great as some titanium alloys. Unfortunately, ceramic materials are very brittle and ceramic end effectors would be susceptible to breakage during normal handling, set-up and operation.

In addition to providing longer end effectors, it may be desired to improve the acoustical transmission efficiency of the end effector in order to reduce "self-heating" of the end effector and the time to cut and coagulate tissue. Some materials such as sapphire, titanium and aluminum may transmit ultrasonic energy more efficiently than other materials such as copper and steel. Acoustical transmission efficiency of surgical ultrasonic end effectors may be associated with a unitless acoustical coefficient, known in the art as the "Q" coefficient, which for the Ti-6Al-4V titanium alloy and some aluminum alloys is in the range of 10,000 to 20,000. The Q coefficient for certain steels may be as low as 250. For applications in which self-heating of the end effector should be minimized, the end effector may be formed from a material having a high Q coefficient. However, there may be some surgical applications in which rapid self-heating of the end effector is desired, such as when the end effector is used while immersed in body fluids. For such applications, the end effector may be formed from a material having a lower Q coefficient in order to quickly generate heat in the tissue to cut and coagulate the tissue.

The thermal conductivity of the end effector material may also significantly affect how quickly the end effector cuts and coagulates tissue. If the end effector conducts heat to the tissue too quickly, the tissue may char. But if the end effector conducts heat to the tissue too slowly, the device may cut and/or coagulate too slowly. Depending on the surgical application, an end effector formed from the Ti-6Al-4V alloy, which has a thermal conductivity of about 7 W/m-K, may retain too much heat, whereas an end effector formed from aluminum, which has a thermal conductivity of about 200 W/m-K, may pull too much heat away from the tissue.

The mechanical fatigue strength of the end effector material may significantly affect the operational life of the end effector and, consequently, how many times the end effector can be used during a surgical procedure. Fatigue strength is sometimes referred to as the endurance limit of the material and corresponds to the stress at which the material may be reversibly stressed for practically an infinite number of cycles. The Ti-6Al-4V alloy has a fatigue strength of about 413 kPa, whereas the fatigue strength of aluminum is about 138 kPa. Aluminum also is softer than the titanium alloy and is more easily damaged by other surgical instruments during usage, possibly leading to crack initiation that may further reduce the fatigue resistance of the end effector.

Clearly, the design of surgical ultrasonic end effectors has been very challenging at least in part because the available choices for a single end effector material that has the combination of acoustical and mechanical characteristics desired for certain surgical applications is very limited. For example, it may be desired to provide a surgical ultrasonic end effector that has a longer ultrasonic propagation wavelength and a greater fatigue strength than current end effectors, and yet maintains the acoustic efficiency and thermal characteristics of current end effectors.

Another surgical instrument is disclosed by U.S. Pat. No. 6,375,635 which uses a liquid jet for cutting tissue. The instrument includes a pressure lumen that conducts a high pressure liquid towards a distal end of the instrument and that includes a nozzle that provides a jet opening. The instrument further includes an evacuation lumen opposite the jet opening to receive a liquid jet when the instrument is in operation.

SUMMARY

In an aspect, an ultrasonic surgical system includes an ultrasonic transmission member having a proximal end and a distal end. An ultrasonically actuated end-effector is attached at the distal end of the transmission member. A pressurized fluid delivery system includes a fluid nozzle in communication with at least one fluid source. The fluid nozzle is arranged and configured to deliver pressurized fluid to soft tissue at a rate to move the soft tissue away from the end-effector during use.

In another aspect, an ultrasonic surgical system includes an ultrasonic transmission member and an ultrasonically actuated end-effector attached to the transmission member. A sheath is moveable relative to the end-effector. The sheath has a first configuration in which the sheath covers the end-effector to inhibit interaction with tissue by the end-effector and a second configuration in which the end-effector is exposed beyond the sheath to interact with tissue.

In a third aspect, a method of treating tissue using an ultrasonic surgical system is provided. The method includes locating an ultrasonically actuated end-effector attached at a distal end of an ultrasonic transmission member in proximity to tissue. Pressurized fluid is directed onto soft tissue at a rate to move the soft tissue away from the end-effector using a pressurized fluid delivery system including a fluid nozzle in communication with at least one fluid source.

In a fourth aspect, an ultrasonic surgical system includes a surgical instrument having a distal end adapted to perform a surgical procedure on a patient and a proximal end adapted to be controllable by an operator. The instrument includes a pressure lumen having sufficient burst strength to conduct a high pressure liquid towards the distal end of the instrument. The pressure lumen includes at least one nozzle providing a jet opening. The nozzle is shaped to form a liquid jet as a liquid at high pressure flows therethrough. An evacuation lumen includes a jet-receiving opening having a cross-sectional area and locatable opposite the jet opening at a predetermined distance therefrom to receive a liquid jet when the instrument is in operation and to deliver the liquid from the surgical site in the form of a liquid column. An ultrasonic system is configured to impart ultrasonic energy to one or more of the pressure lumen, liquid jet, evacuation lumen and liquid column.

In a fifth aspect, an ultrasonic surgical system includes an ultrasonic transmission member having a proximal end and a distal end, An ultrasonically actuated end-effector is attached at the distal end of the transmission member. The end-effector is a composite end-effector comprising diamond particles disposed in a matrix of metal material. The diamond particles are exposed at a surface of the end-effector for contact with tissue during use.

The details of one or more embodiments of the invention are set forth in the accompanying drawings and the description below. Other features, objects, and advantages of the invention will be apparent from the description and the drawings, and from the claims.

BRIEF DESCRIPTION OF THE FIGURES

FIGS. 5 and 6 are partial, side section views of the ultrasonic surgical instrument of FIG. 4 in an extended and a retracted configuration, respectively;

FIG. 16 is a perspective view of an embodiment of an ultrasonic transmission assembly;

FIG. 17 is a section view of the ultrasonic transmission assembly along line 17-17 of FIG. 16;

DETAILED DESCRIPTION

Before explaining the present invention in detail, it should be noted that the invention is not limited in its application or use to the details of construction and arrangement of parts illustrated in the accompanying drawings and description. The illustrative embodiments may be implemented or incorporated in other embodiments, variations and modifications, and may be practiced or carried out in various ways. Furthermore, unless otherwise indicated, the terms and expressions employed herein have been chosen for the purpose of describing the illustrative embodiments for the convenience of the reader and are not for the purpose of limiting the invention.

Figure 1:
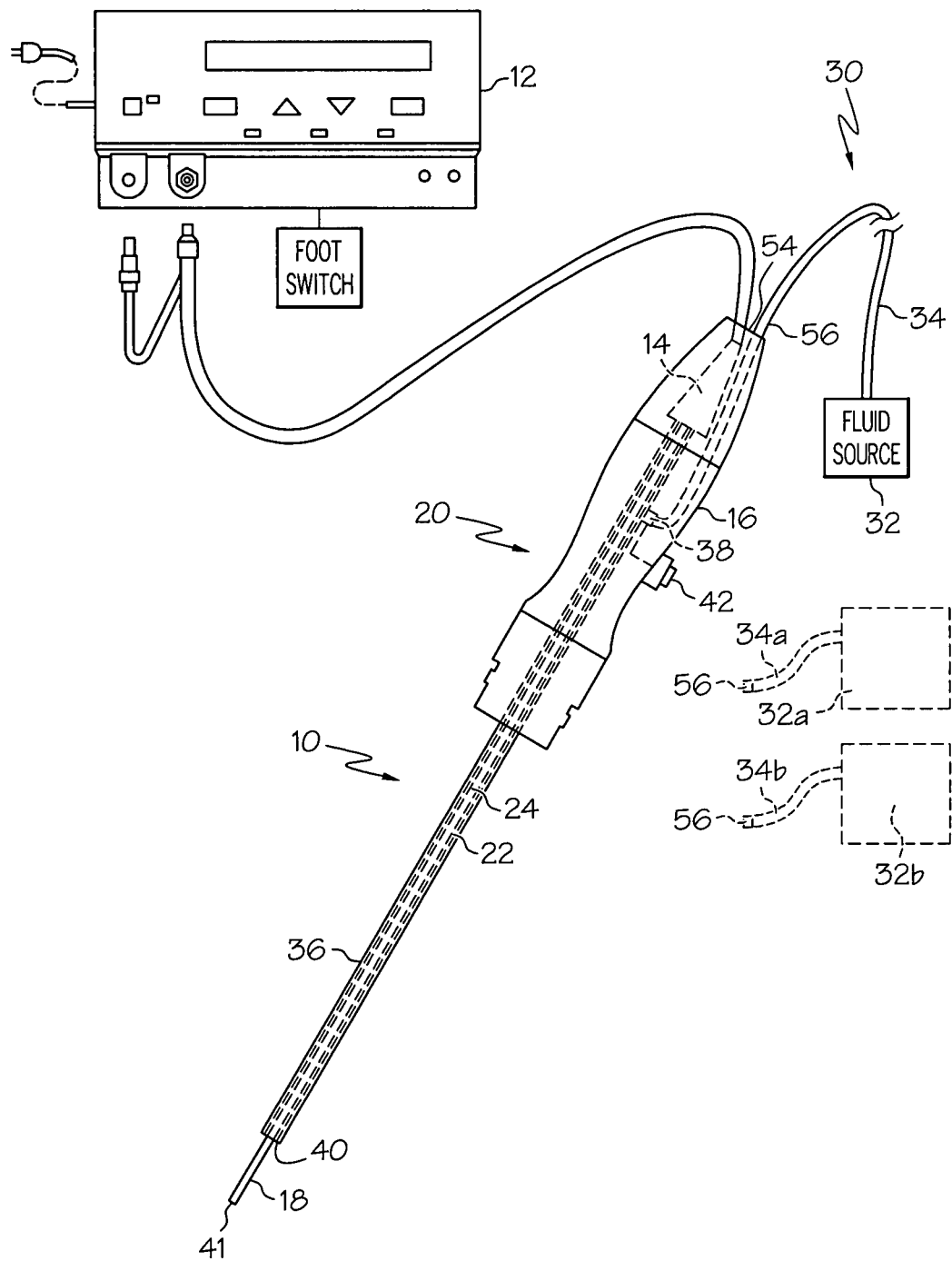
FIG. 1 illustrates an embodiment of a ultrasonic surgical instrument capable of delivering pressurized fluid.

Referring to FIG. 1, an exemplary ultrasonic system 10 comprises an ultrasonic signal generator 12 with ultrasonic transducer 14 and hand piece housing 16. Ultrasonic transducer 14 converts the electrical signal from ultrasonic signal generator 12 into mechanical energy that results in primarily longitudinal vibratory motion of the ultrasonic transducer 14 and an ultrasonic end-effector 18 at ultrasonic frequencies. A suitable generator is available as model number GEN04, from Ethicon Endo-Surgery, Inc., Cincinnati, Ohio. When acoustic assembly 20 is energized, a vibratory motion standing wave is generated through the acoustic assembly 20. The distal tip of the ultrasonic end-effector 18 may vibrate in the longitudinal direction with a peak-to-peak amplitude of approximately 10-200 microns at an ultrasonic frequency of 55.5 kHz. An elongated inner sheath 22 retains a waveguide 24 and the proximal end of ultrasonic end-effector 18. The amplitude of the vibratory motion at any point along the acoustic assembly 20 depends on the location along the acoustic assembly at which the vibratory motion is measured. A minimum or zero crossing in the vibratory motion standing wave is generally referred to as a node (i.e., where longitudinal motion is usually minimal), and an absolute value maximum or peak in the longitudinal standing wave is generally referred to as an antinode. In some embodiments, the distance between an antinode and its nearest node is one-quarter wavelength ($\lambda/4$).

The components of the acoustic assembly 20 may be acoustically tuned such that the length of any assembly is an integral number of one-half wavelengths ($n\lambda/2$), where the wavelength $\lambda$ is the wavelength of a pre-selected or operating longitudinal vibration drive frequency $f_d$ of the acoustic assembly 20, and where n is any positive integer. It is also contemplated that the acoustic assembly 20 may incorporate any suitable arrangement of acoustic elements. Details for imparting vibratory motion to an end effector are described in, for example, U.S. Pat. Nos. 6,254,623, 6,976,969, 7,163,548 and U.S. patent application Ser. No. 11/246,826 entitled "Actuation Mechanism For Use With An Ultrasonic Surgical Instrument," filed Oct. 7, 2005, the details of all of which are hereby incorporated by reference as if fully set forth herein.

Referring still to FIG. 1, ultrasonic system 10 further includes a fluid delivery system 30. Fluid delivery system 30 includes a pressurized fluid source 32 (e.g., including a pump, compressor, etc.), a conduit 34 for directing pressurized fluid from the pressurized fluid source to the hand piece housing 16. Conduit 34 is connected to an outer sheath 36 by a valve 38 (e.g., a solenoid valve). Outer sheath 36 has an inner diameter that is greater than an outer diameter of the inner sheath 22, forming a fluid passageway therebetween through which pressurized fluid can travel. The fluid passageway is in communication with a fluid outlet 40 located at a distal end of the outer sheath 36. In the illustrated embodiment, fluid outlet 40 forms a nozzle that is located proximally to a distal end 41 of the end-effector 18.

In some embodiments, the ultrasonic system 10 includes a control (in this instance, in the form of button 42) that allows for user control of fluid delivery. As illustrated, the button 42 is located on the hand piece housing 16. As one example, depressing the button 42 (e.g., using a user's finger) sends a signal to valve 38 which causes the valve to open, allowing fluid to enter the fluid passageway between the inner and outer sheaths 22 and 36. When the button 42 is released, the signal is discontinued and the valve 38 closes, thereby preventing fluid from entering the fluid passageway. Other examples are contemplated. For example, the control 42 may be connected to a controller (not shown) that controls operation of the valve based on an input from the control. Control 42 may include multiple inputs (e.g., buttons, switches, dials, etc.) corresponding to multiple settings that allows for user control of a number of fluid delivery parameters. As one example, the fluid delivery system 30 may include multiple fluid sources of different fluid types (e.g., liquid and gas). Control 42 may allow for user selection of the different fluid types or a combination of pressurized fluid types for delivery through the fluid passageway toward the fluid outlet 40. In another embodiment, the button 42 may be a push button mechanical valve that can be opened and closes by pressing and releasing the button.

In an alternative system embodiment, the ultrasonic system 10 does not include the inner sheath 22 and the fluid passageway is formed using the outer sheath 36, the pressurized fluid flowing between the waveguide 24 and the outer sheath. In another system embodiment, a central lumen (element 35) extending through the waveguide 24 and the ultrasonic end-effector 18 is used to deliver the pressurized fluid.

As another example, multiple pressurized fluid sources 32a and 32b may be provided as illustrated by the dotted lines, where each pressurized fluid source provides a different type of fluid. For example, fluid source 32a may provide air (or other gas) and fluid source 32 may provide saline (or other liquid). In some embodiments, the fluid sources 32a and 32b may provide fluid at different pressures. In one embodiment, hand piece housing 16 may include a connect/disconnect port 54 capable of mating with a connector 56 (e.g., threaded, friction fit, etc. forming a fluid-tight seal) located at ends of conduits 34a and 34b. The user may select between the different fluid types by connecting the desired pressurized fluid source 32a, 32b to the port 54 and, in some instances, disconnecting the undesired pressure fluid source.

Figure 2A:
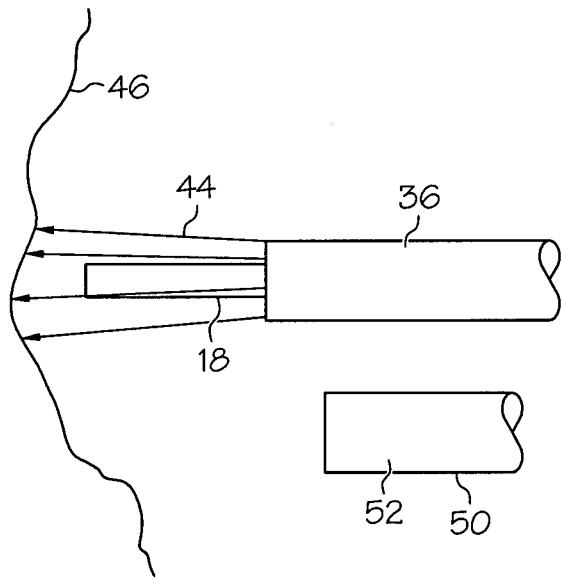
FIGS. 2a and 2b illustrate a detail view of a distal end of the surgical device of FIG. 1 in use.
Figure 2B:
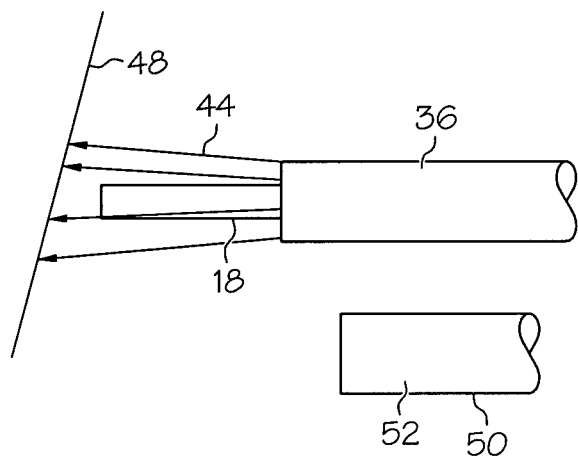

Referring now to FIGS. 2a and 2b, pressurized fluid jets 44 can be directed past the end-effector 18 to nearby soft tissue 46 at a rate that displaces the soft tissue. FIG. 2a represents soft tissue 46 being displaced and FIG. 2b represents soft tissue 46 displaced using the pressurized fluid to expose bone 48. Displacing the soft tissue 46 may be advantageous, for example, when treatment of harder material, such as bone 48 is desired while avoiding injury to the soft tissue. In orthopedic surgery for example, such as surgery of the spine, there may be a need to cut bone while avoiding the cutting of surrounding soft tissue using end-effector 18. Directing fluid by the end-effector 18 may provide an additional advantage of cooling the end-effector 18 during use.

The rate at which the fluid is delivered to move soft tissue 46 without injuring the tissue may depend on several factors such as the desired tissue displacement amount, type of surrounding tissue, amount of tissue being displaced and the type of fluid and fluid pressure. Rate of the fluid may be controlled by a combination of outlet 40 size and pressure. In some embodiments, saline may be the fluid used and delivered at between about 20 ml/sec and 100 ml/sec, such as at about 50 ml/sec. In another embodiment, air may be the fluid used and delivered at between about 5 psi and 20 psi, such as at about 10 psi. In some implementations, control 42 (FIG. 1) may allow for pressure adjustment by the user by providing a tunable pressure system, which allows for user adjustment of the fluid outlet rate. In another embodiment, pressure adjustment may be capable at the pressurized fluid source.

In some embodiments, a suction system 50 may be used in conjunction with the fluid delivery system 30. Suction system 50 may be separate from the ultrasonic system 10, as shown, or the suction system may be attached or a part of the ultrasonic system. Suction system 50 includes a suction lumen 52 that is connected to a vacuum source (not shown) capable of generating a negative pressure within the suction lumen. Suction system 50 is used to draw fluid and/or debris away from the treatment site during use.

Figure 3:
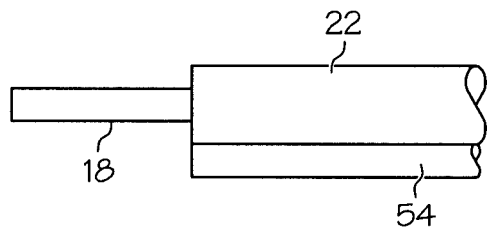
FIG. 3 illustrates another embodiment of an ultrasonic surgical instrument capable of delivering pressurized fluid.

While a coaxial design is shown by FIGS. 1-2b where the outer sheath 36 surrounds and coextends with inner sheath 22, other embodiments are contemplated. For example, FIG. 3 illustrates an embodiment where a high pressure conduit 54, adjacent sheath 22 is used to deliver pressurized fluid to displace soft tissue. In another embodiment, multiple high pressure conduits 54 may be used to deliver pressurized fluid to displace soft tissue. As further alternatives, suction may be provided between the inner and outer sheaths 22 and 36, between the ultrasonic end-effector 18 and the outer sheath 36 or through a lumen (not shown) formed through the end-effector.

Figure 4:
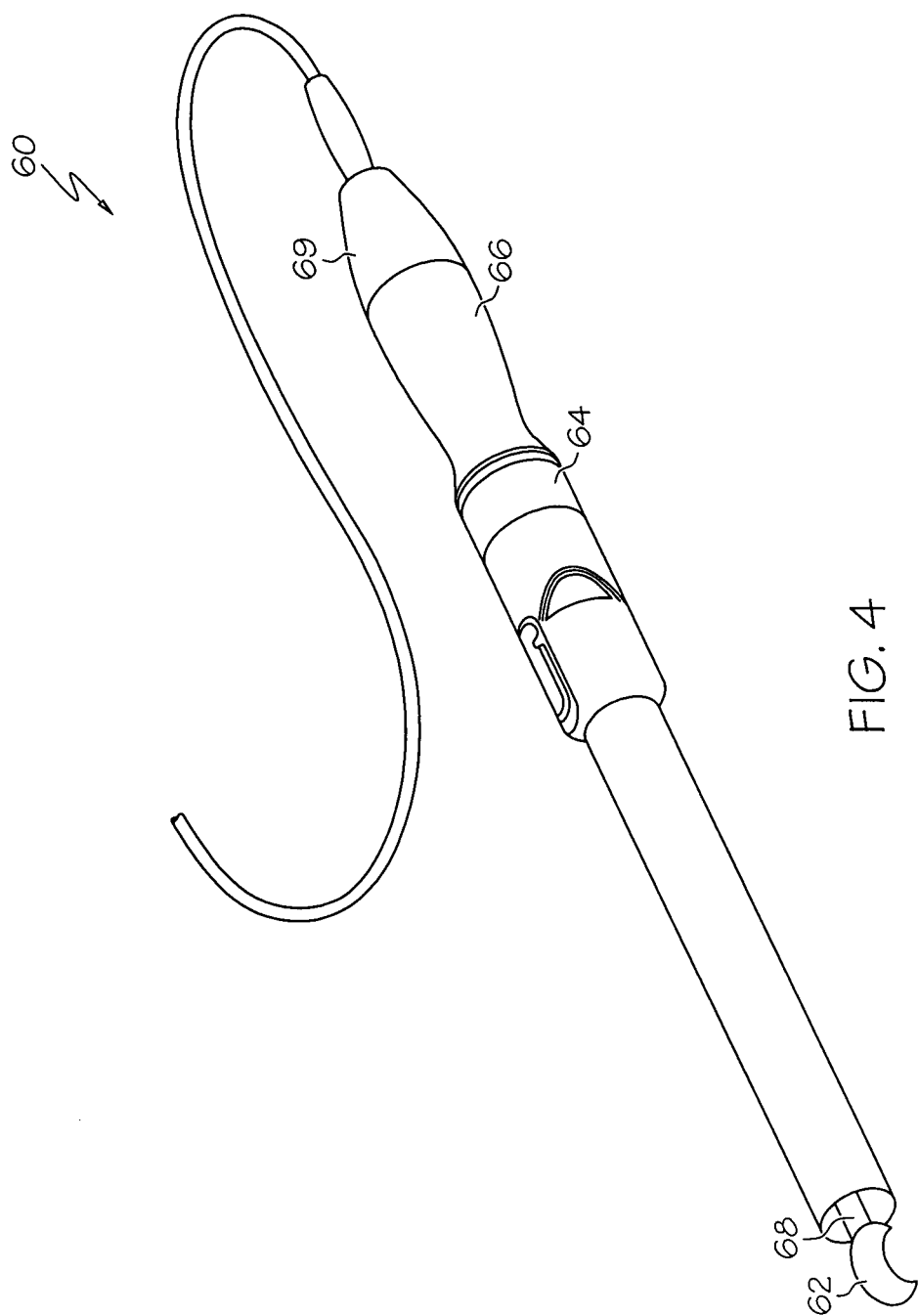
FIG. 4 is a perspective view of another embodiment of an ultrasonic surgical instrument including a moveable sheath assembly.

FIG. 4 illustrates another embodiment of an ultrasonic system 60 capable of displacing soft tissue. Ultrasonic system 60 is merely exemplary as other systems may be employed. The ultrasonic system 60 includes an end-effector 62, hand piece 64, instrument handle 66 and ultrasonic transmission rod assembly 68. Hand piece 64 includes an ultrasonic transducer 69 (e.g., a piezoelectric transducer) for converting an electrical signal (e.g., a 55,000 Hz sinusoidal waveform) from a signal generator into a mechanical vibration. An exemplary signal generator is an Ultracision® model HP054, commercially available from Ethicon Endo-Surgery, Inc. End-effector 62 may be a dissecting hook such as that provided by model DH105, also available from Ethicon Endo-Surgery, Inc.

Referring now to FIG. 5, ultrasonic system 60 includes a moveable sheath assembly 70 that includes a connector component 72 that is fixed to waveguide 74 at a fixed node 76. Waveguide 74 includes a mounting segment 78 that is received within an annular channel 80 of the connector component 72 to inhibit axial movement of the connector component relative to the waveguide. Connector component 72 includes an axial portion 82 that includes the annular channel 80 and a radial portion 84. Radial portion 84 forms a stop for the moveable sheath assembly 70.

A moveable component 86 is slidingly connected to the connector component 72. Moveable component 86 includes a distal portion 88 that is located distally of the connector component 72 and a proximal portion 90 that is located proximally of the connector component. Radial portion 84 is received within a slot 92 formed in an inner surface 94 of the moveable component 86. The slot 92 extends axially to allow for axial movement of the moveable component relative to the connector component 72.

A biasing member 96 (in this embodiment, a spring) is located between the connector component 72 and the moveable component 86. Biasing member 96 seats against a radially extending seating surface 98 of the moveable component 86 and the radial portion 84 of the connector component 72. Radially extending seating surface 98 defines a distal end to the slot 92. Biasing member 96 biases the moveable component 86 toward an extended configuration as illustrated by FIG. 5. In the extended configuration, the moveable component 86 extends distally beyond the end-effector 62. A radially extending seating surface 100 inhibits further axial movement of the moveable component 86 due to the biasing force applied by the biasing member 96 by engaging the radial portion 84 of the connector component 72. Seating surface 100 forms a proximal end to the slot 92.

FIG. 6 illustrates the moveable sheath assembly 70 in a retracted configuration where a force F overcomes the axial biasing force applied by the biasing member 96 to the moveable component 86. This force F causes axial movement of the moveable component 86 proximally relative to the waveguide 74 and connector component 72 with the slot 92 moving relative to the radial portion 94 of the connector component. The slot 92 is sized to allow sufficient axial movement of the moveable component 86 such that the end-effector 62 is exposed beyond a distal end 102 of the moveable component.

Figure 7:
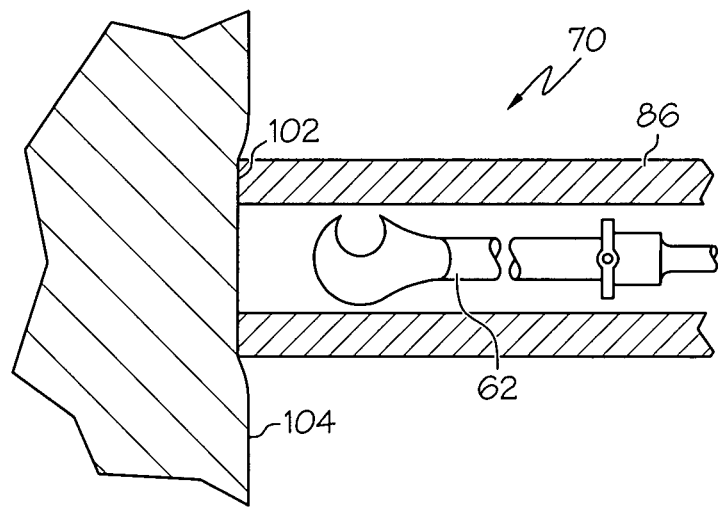
FIG. 7 is a partial, detail side section view of a distal end of the ultrasonic surgical instrument of FIG. 5 in contact with tissue.
Figure 8:
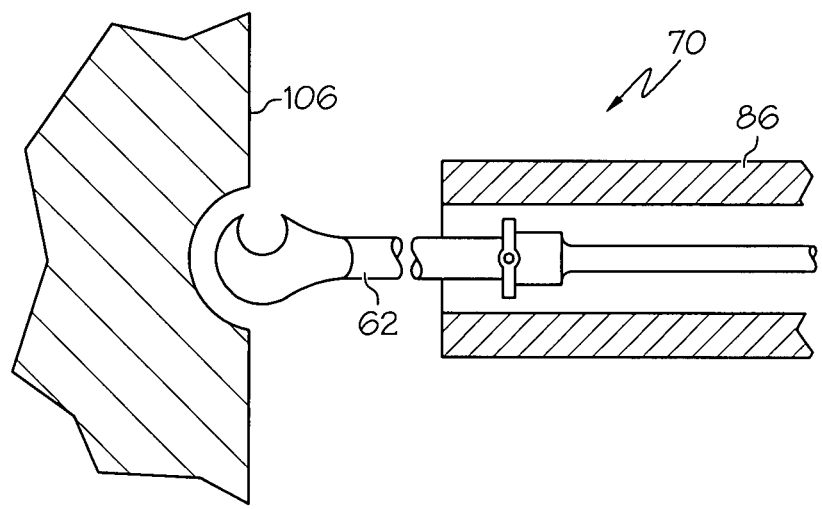
FIG. 8 is a partial, detail side section view of a distal end of the ultrasonic surgical instrument of FIG. 6 in a retracted configuration to cut bone.

The desired biasing force provided by the biasing member 96 to the moveable component 86 to move soft tissue 46 without injuring the tissue may depend on several factors such as the desired tissue displacement amount, type of surrounding tissue, amount of tissue being displaced, etc. The biasing force should be selected, however, such that the moveable component 86 retracts axially under, for example, a manually applied force, when the distal end 102 contacts a relatively hard material such as bone. FIG. 7, for example, illustrates the moveable sheath assembly 70 in the extended configuration with the distal end 102 of the moveable component 86 located distally of the end-effector 62 and in contact with soft tissue such as dura 104, displacing the tissue as the distal end of the moveable component 86 is moved forward. When the distal end 102 contacts relatively hard material such as bone 106, continued forward movement of the instrument causes the end-effector 62 to extend beyond the distal end 102, exposing the end-effector and placing the moveable sheath assembly in the retracted position as shown by FIG. 8. When the instrument is moved away from the bone 106, the end-effector 62 moves relative to the moveable component 86, retracting back into the moveable component.

Figure 9:
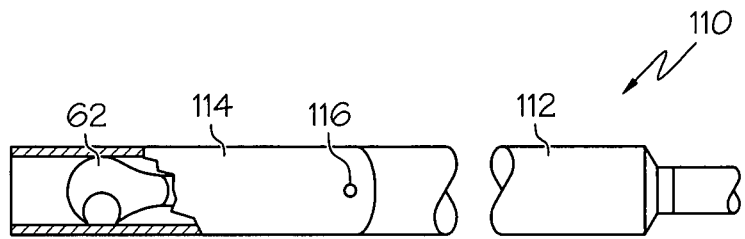
FIGS. 9-11 are partial views of another embodiment of an ultrasonic surgical instrument including a moveable sheath assembly.

Referring to FIG. 9, an alternative embodiment of a moveable sheath assembly 110 includes a connector component 112 that is connected to the waveguide (e.g., in a fashion that is similar to the connector component 72) and a moveable component 114 that is rotatably connected to the connector component 112. The moveable component 114 is rotatably connected to the connector component 112 by, in this embodiment, a pin 116 that defines a pivot axis about which the moveable component 114 can rotate. A biasing member (not shown, such as a torsional spring) may be used to bias the moveable component 114 toward an undeflected configuration as shown by FIG. 9. As an alternative, the moveable component material may be selected to have sufficient flexural stiffness such that the moveable component 114 itself can be used as a cantilever spring to bias the moveable component toward the undeflected configuration.

Figure 10:
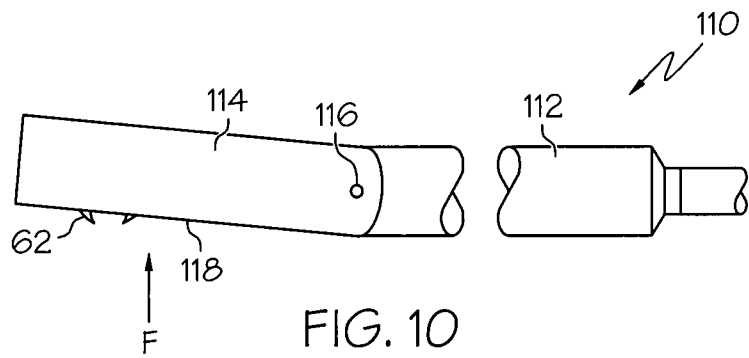
Figure 11:
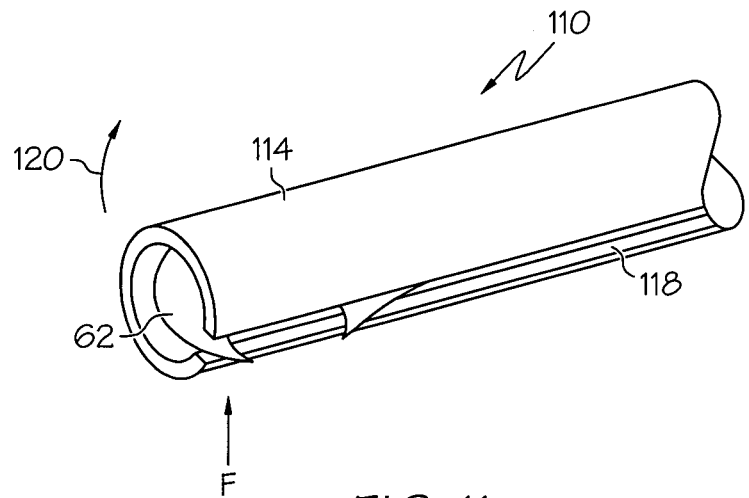

Referring now to FIGS. 10 and 11, the moveable component 114 includes a slot 118 that is sized to allow the end-effector 62 to pass therethrough. Referring particularly to FIG. 11, when a force F is applied to the moveable component 114 that is sufficient to overcome the biasing force, the moveable component rotates in the direction of arrow 120. The location and size of the slot 118 allows the end-effector 62 to pass therethrough as the moveable component 114 rotates until the end-effector is exposed, for example, for a cutting operation. As above, the biasing force provided by the biasing member to the moveable component 114 may be selected to move soft tissue without injuring the tissue and to allow rotation of the moveable member 114, for example, using a manually applied force, when the moveable component 114 contacts a relatively hard material such as bone.

Figure 12:
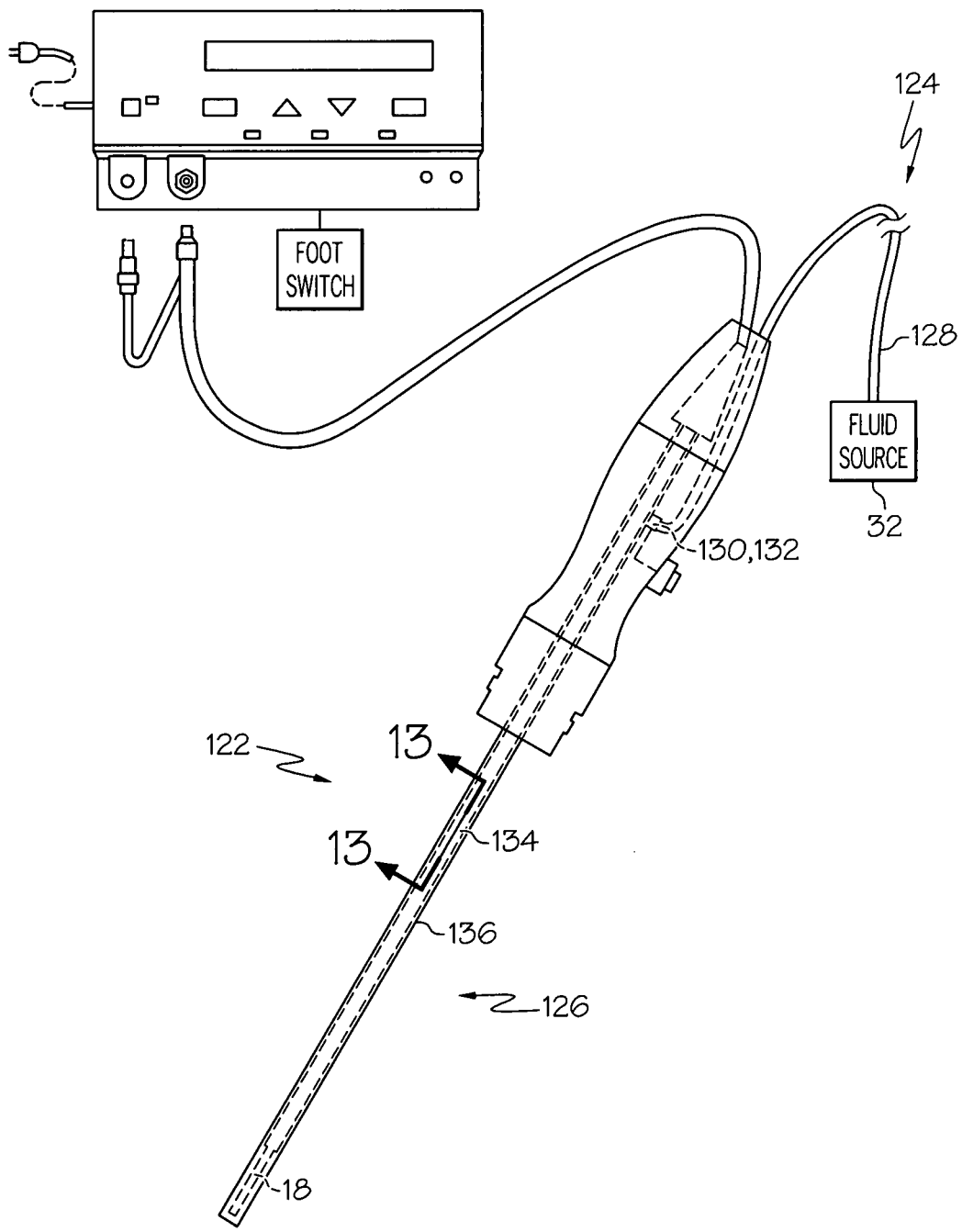
FIG. 12 illustrates another embodiment of an ultrasonic surgical instrument including a pressurized fluid delivery system and a moveable sheath assembly.

Referring to FIG. 12, some of the above-described features are combined in ultrasonic system 122. The ultrasonic system 122 includes both a fluid delivery system 124 and a moveable sheath assembly 126. Fluid delivery system includes fluid source 32 and a conduit 128 that is coupled to a fluid inlet 130, for example, using a valve 132. Moveable sheath assembly 126 includes a connector component 134 and a moveable component 136 slidably connected thereto. As above with moveable component 114, moveable component 136 can retract relative to the end-effector 18 to expose the end-effector, for example, for a cutting operation.

Figure 13:
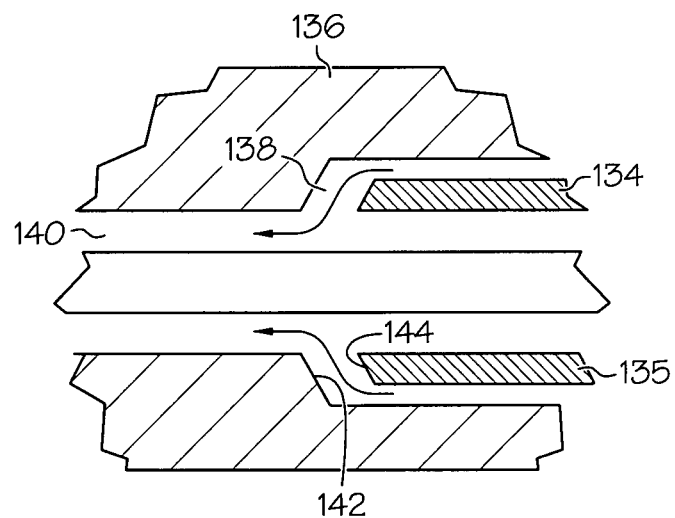
FIGS. 13 and 14 are side section views of the ultrasonic surgical instrument along line 13-13 of FIG. 12 in extended and retracted configurations, respectively.
Figure 14:
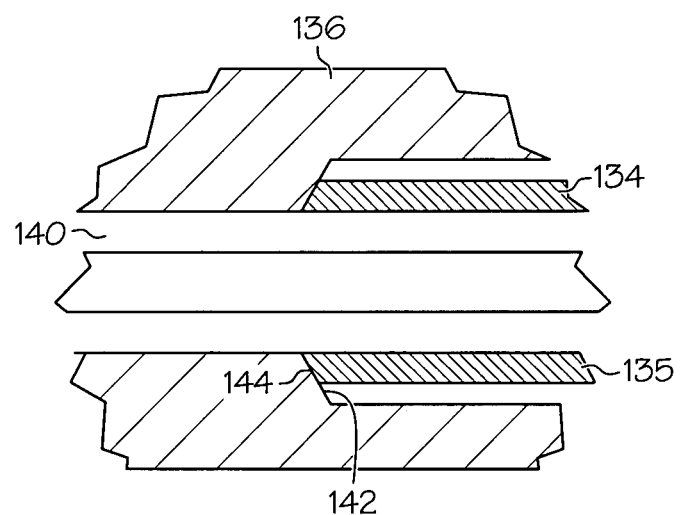

FIGS. 13 and 14 illustrate the moveable component 136 in its extended (FIG. 13) and retracted (FIG. 14) configurations. As can be seen by FIG. 13, in the extended configuration, a fluid opening 138 is formed between the axial portion 135 of the connector component 134 and the moveable component 136. The fluid opening 138 allows pressurized fluid to flow into the fluid passageway 140 toward a fluid outlet. In some embodiments, the pressurized fluid may be used to provide a biasing force to the moveable component 136 to bias the moveable component toward its extended position. FIG. 14 shows the moveable component 136 in its retracted configuration. In the retracted configuration, surface 142 of the moveable component 136 engages surface 144 of the connector component 134, thereby closing fluid opening 138 and forming a seal that inhibits fluid flow into the fluid passageway 140. As can be appreciated, in this embodiment, the moveable and connector components 136 and 134 form a mechanical valve that allows for control of fluid flow to the fluid outlet. In some implementations, the mechanical valve formed by the moveable and connector components 136 and 134 may provide progressive control of pressurized fluid flow through the adjustment of fluid opening 138 size. This can allow for adjustment of fluid flow between a "full on" flow rate and a "full off" flow rate.

In another embodiment, the moveable component 136 is adjusted manually thereby forming a manually adjustable mechanical valve where the user can manually control the size of the fluid opening 138. In yet another embodiment, the moveable component 136 is used to cut off flow with the moveable sheath in the extended position, which would allow fluid flow only when the sheath is retracted (e.g., during cutting).

Figure 15B:
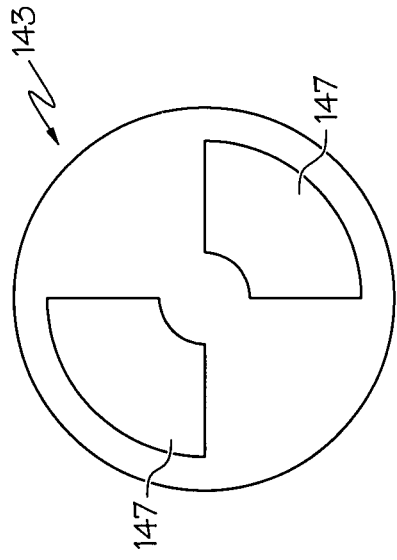
FIG. 15 is a section view of another embodiment of an ultrasonic surgical instrument.
Figure 15D:
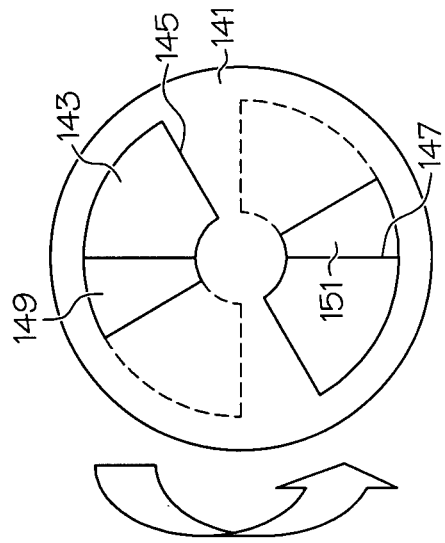
Figure 15A:
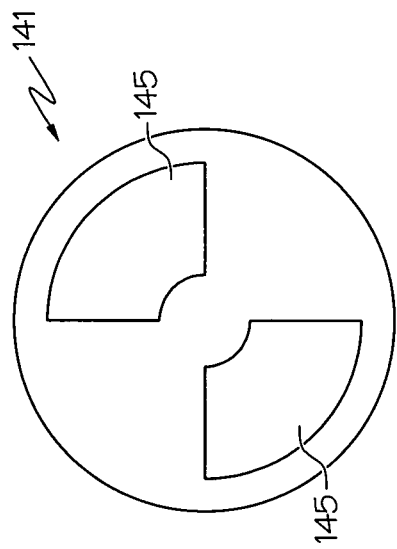
Figure 15C:
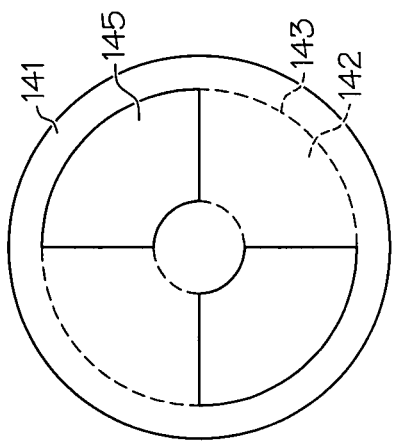

FIGS. 15A-15D illustrate an exemplary embodiment that includes an adjustable mechanical valve that can be opened and closed by turning one or both components 141 and 143 relative to the other. The components 141 and 143 include fluid passageways 145 and 147, respectively, that are used to deliver fluid to the fluid outlet. FIG. 15C illustrates the components 141 and 143 connected in a closed configuration with their respective passageways 145 and 147 rotated 90 degrees relative to each other. FIG. 15D illustrates the components 141 and 143 being rotated relative to each other, thereby opening fluid flow paths 149 and 151.

Referring back to FIGS. 1-14, the end-effector 18 and 62 and associated waveguide may be unitarily formed from a titanium alloy such as Ti-6Al-4V, an aluminum alloy, or from any other suitable material. Alternately, the end-effector may be formed separately from the same material as waveguide, or from an alternate material. The end-effector then may be attached to waveguide by a threaded connection or by a welded joint, for example. As is well-known in the art, the proximal end of end effector may be located near the most distal, vibratory nodal point of waveguide. The distal end of the end effector corresponds to the location of a vibratory anti-nodal point. The length of the end effector, therefore, is approximately equal to one quarter of the acoustic wavelength that is characteristic of the material composition of the end-effector for a particular ultrasonic energy input frequency. For example, when the end effector is formed from Ti-6Al-4V, the characteristic wavelength is approximately 87 mm, and the length of the end effector is approximately 22 mm.

However, it may be desirable to form the end-effector 18, 62 from a combination of materials, thereby providing a composite end-effector. Referring now to FIG. 16, a perspective view of the distal portion of a first embodiment of an ultrasonic transmission assembly 150 for an ultrasonic surgical instrument is shown. FIG. 17 is a cross-sectional view of assembly 150 taken at line 17-17 of FIG. 16. Assembly 150 includes a waveguide 152 that may be similar to the waveguide described above. The distal end of waveguide 152 attaches to the proximal end of a composite end-effector 154 near a first vibratory nodal point 156. Nodal point 156 may also be positioned slightly proximal to the proximal end of end-effector 154. The ordinate system shown in FIG. 16 defines a longitudinal axis 158 of assembly 150 to be parallel to the z-axis. Composite end-effector 154 includes a cylindrical, first portion 160 having a circular cross-section. First portion 160 has a bore 162 (also referred to as a cavity) coaxial to longitudinal axis 158 and extending between the distal and proximal ends of end-effector 154. A cylindrical, second portion 164 may be positioned inside of bore 162 and may substantially fill bore 162. It should be noted that although the bore 162 in the first portion 160 is shown to extend to near a vibratory nodal point 156, alternative embodiments of this approach allow for the bore 162 to extend and fraction of single or multiple wavelengths through the material, up to and including through the entire waveguide 152.

First portion 160 may be formed from a first material, which may be any one of a number of suitable materials, including a titanium alloy such as Ti-6Al-4V and an aluminum alloy such as 7075-T6. First portion 160 provides a relatively tough, outer covering to second portion 164 to resist structural stresses during normal handling, set-up and operation of the ultrasonic surgical instrument. First portion 160 characteristically (wherein "characteristically" refers to the acoustic properties normally exhibited by the material) vibrates, for example, with a first wavelength when excited by an ultrasonic energy input, such as may be provided by the ultrasonic drive unit of the ultrasonic surgical instrument. An example of an ultrasonic energy input is approximately 3 watts at a frequency of about 55.5 kHz. An example of a first wavelength is approximately 87 mm.

Second portion 164 is formed from a second material, which may be any one of a number of suitable materials, including alumina, aluminum nitride, zirconia, silicon carbide, silicone nitride, sapphire and ruby. Second portion 164 may extend only a portion or the entire length of end-effector 154. Second portion 164 characteristically vibrates, for example, with a second wavelength when separately excited by the ultrasonic energy input. The second wavelength may be substantially greater than the first wavelength of first portion 160. An example of a second wavelength is approximately 174 mm.

First portion 160 and second portion 164 may be joined together using any one or a combination of a number of suitable processes, including but not limited to, brazing, fritting and mechanically coupling. When first portion 160 and second portion 164 are joined together and excited by the ultrasonic energy input, composite end-effector 154 characteristically vibrates with a composite wavelength that is between the first and second wavelengths.

Similarly, one or more of other material properties, including thermal conductivity, ultrasonic power transmission efficiency and fatigue strength of end-effector 154 may have composite characteristic values. Furthermore, each composite characteristic value associated with a material property may be in a range defined by the characteristic values for that material property of first portion 160 and second portion 164.

For example, in some embodiments, material forming first portion 160, such as a titanium alloy may be chosen having a relatively low thermal conductivity and material forming second portion 164, such as an aluminum alloy may be chosen having a relatively high thermal conductivity. In one embodiment, second portion 164 may be between about 30 to 70 percent (e.g., about 50 percent) of an overall width W of the end-effector 154 with first portion 160 making up the remainder of the width W. This exemplary arrangement should provide a composite heat transfer coefficient somewhere between that of end-effectors made from either of the materials alone. Advantageously, an end-effector may be provided that is capable of transferring heat away from the tissue in the active area, but not so fast that rapid tissue transactions are not possible.

As shown in FIG. 17, second portion 164 may have a uniform diameter along its entire length. In other implementations, the second portion 164 and or the first portion 160 may taper in diameter uniformly or even relative to each other. First portion 160 and second portion 164 may be joined together with a tight bond and with minimal gaps in the entire area between the interfacing surfaces to ensure consistently optimal performance of composite end-effector 154. A method for making composite end-effector 154 may include providing a first rod formed from a first material such as a titanium alloy and creating a longitudinal bore extending between the proximal and distal ends of the first rod, such as by a drilling process. For example, the first rod may have an outer diameter of about five millimeters and the longitudinal bore may have a diameter of about four millimeters. The method may further include providing a second rod formed from a second material, such as man-made sapphire, and sizing the diameter of the second rod to fit tightly inside the longitudinal bore of the first rod. The method may further include joining the first rod to the second rod by a joining process. The joining process may be, for example, a fritting process, a brazing process, a mechanical process or a combination of such processes.

Fritting and brazing processes are well-known in the cardiac pacemaker industry for making biocompatible, hermetically-sealed, long-lasting, electrical lead "feed-throughs" through the pacemaker housing. Fritting processes include a ceramic-to-metal sealing process that may be used to bond a ceramic, such as 95% alumina or 100% alumina (sapphire), to a metal, such as titanium, stainless steel or molybdenum. The ceramic (such as second portion 164 of end effector 154 in FIG. 17) may be metalized using a powder refractory metal or a thin film sputtered metalizing technique. The metalized ceramic may then be held with high pressure to the metal (such as first portion 160 of end-effector 154 in FIG. 17) and subjected to high heat for a period of time to bond the ceramic and metal together.

It is also possible to braze second portion 164 and first portion 160 together with a brazing alloy (e.g., silver, gold or gold-copper), although such brazing alloys are generally "lossy" (i.e., they do not propagate acoustic energy efficiently and tend to rapidly generate heat) in regards to propagation of an ultrasonic energy input. However, the use of lossy materials in the composition of end-effector 154, including the forming of second portion 164 from a lossy material such as silver, gold, and the like, would potentially allow end-effector 154 to be particularly suitable for use in a fluidic environment. For example, surgeons often use ultrasonic surgical instruments to cut and/or coagulate tissue submerged in body fluids that rapidly dissipate heat from the end effector. Consequently, the time required to cut and/or coagulate tissue is significantly increased, which may be very costly to the patient. Ultrasonic instruments having end-effectors composed of lossy materials and specifically adapted to cut and coagulate tissue even when the end effector is submerged in a body fluid may be provided for such surgical procedures. Combining the self-heating of the lossy material with that of the tissue in contact with the end-effector 154 may allow for the system to provide the necessary heat to denature the proteins in the tissue and cut/coagulate the tissue. Additionally, by utilizing an outer sheath of titanium alloy or other non-lossy alloy around a lossy inner core of material, the amount of self-heating of the composite end-effector can be controlled.

Mechanically joining or coupling second portion 164 to first portion 160 may include press fitting second portion into bore of first portion 160 or mechanically compressing first portion onto second portion. Alternately, a thermal process may be used, for example, in which first portion 160 is heated to increase the diameter of bore before positioning second portion 164 into bore. The assembly may then be permitted to cool so that first portion 160 contracts tightly onto second portion 164. In another embodiment, the first and second portions 160 and 164 are threaded together. Various other well-known mechanical processes may also be used, as is apparent to those skilled in the art.

Those skilled in the art will recognize that a composite end-effector may include a plurality of portions, wherein each portion may have any one of a number of configurations, and the portions may be joined together in any one of a number of arrangements. Each portion may be made of a material that is the same or different than the material of any other portion. Therefore, it is possible to provide a composite end-effector with a desired combination of characteristics related to, but not limited to, composite wavelength when excited by an ultrasonic energy input, structural strength, configuration (including length), mass distribution, manufacturing cost, operating life, heat conduction and heat generation. Each portion may be formed from one of a plurality of materials, wherein each material exhibits a characteristic value of a material property when excited by an ultrasonic energy input, and wherein the composite end effector exhibits a composite characteristic value different from any one of the characteristic values of each material when excited by the ultrasonic energy input.

It is also possible to provide a composite end-effector for an ultrasonic surgical instrument having a plurality of portions formed from a material and joined together such that the composite end effector exhibits an enhanced resistance to fracture propagation through the end effector when excited by the ultrasonic energy input. At least one of the portions may be a laminated portion joined to an adjacent portion such that a fracture initiated in the laminated portion does not propagate through the adjacent portion.

Figure 18:
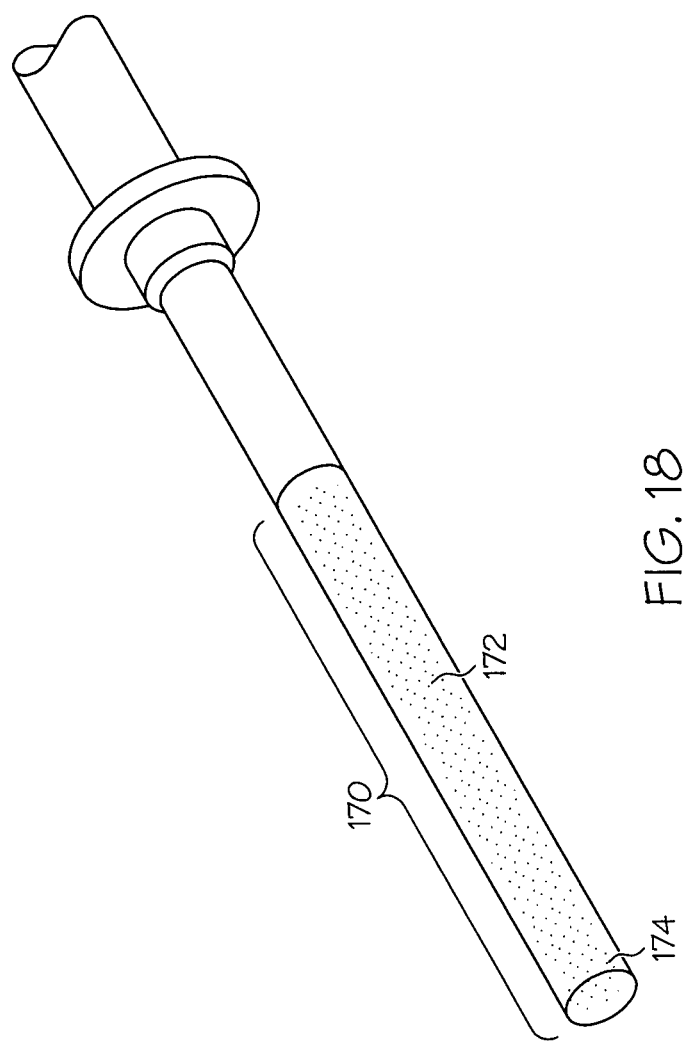
FIG. 18 is a perspective view of another embodiment of an ultrasonic transmission assembly.

Referring now to FIG. 18, in some embodiments, end-effector 170 may include small, hard particles 172, such as diamonds, aluminium oxide particles, etc. disposed in a metal matrix 174 such as a titanium or aluminum alloy that is sintered or hipped. The particles could be applied with an adhesive or as part of a coating. The particles 172 are exposed at the surface of the end-effector 170 so that they can contact the tissue. Addition of the particles 172 increases the abrasion action of the end-effector 170 in contact with tissue. In some implementations, it may be desirable to irrigate the end-effector 170 during use due to the increased abrasion action.

Figure 19:
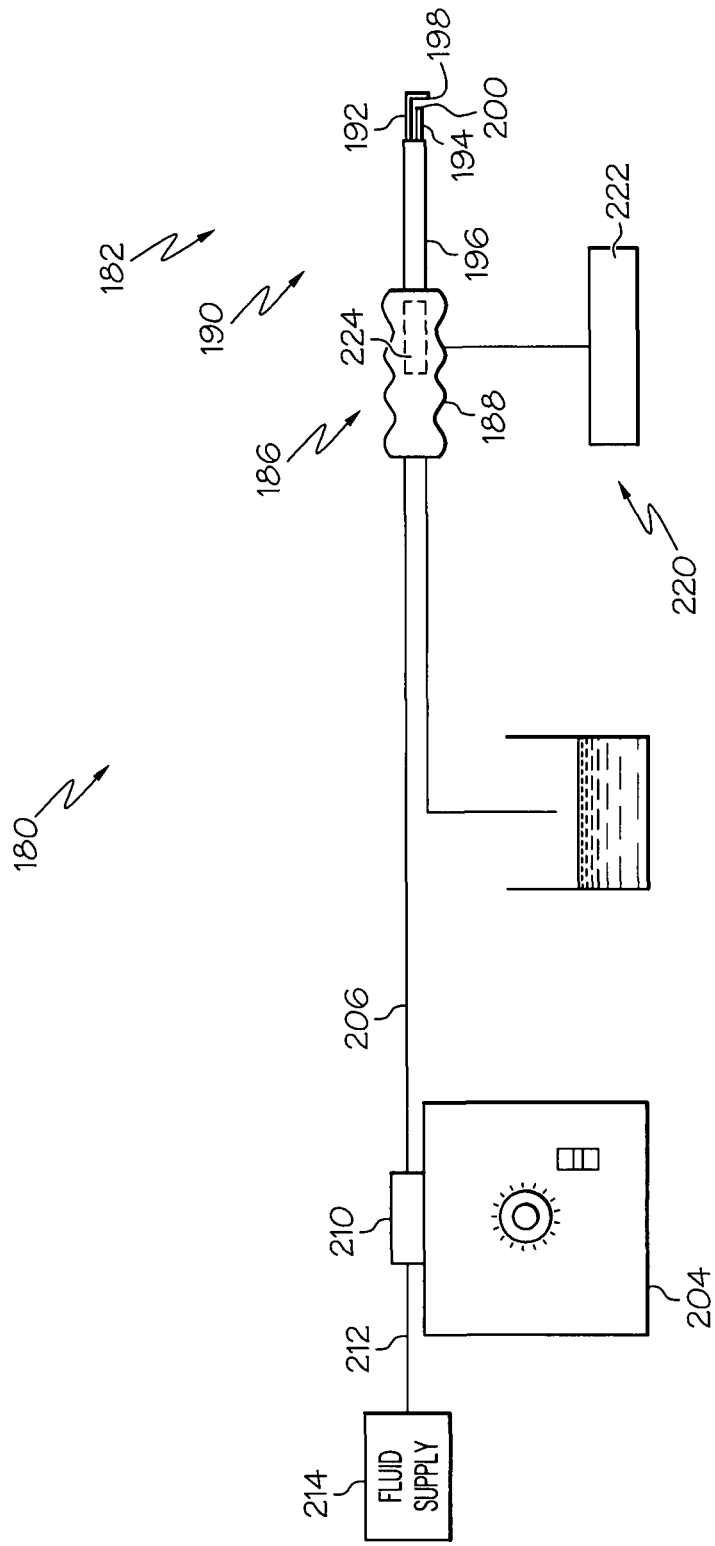
FIG. 19 is a diagrammatic view of another embodiment of an ultrasonic surgical instrument.

Referring to FIG. 19, an embodiment of a liquid jet surgical system 180 is shown. Liquid jet surgical system 180 utilizes a liquid jet surgical instrument 182 that is a surgical handpiece having a proximal end including a body 186 having a grasping region 188 configured for placement in the hand of a user. The surgical instrument 182 has a distal end 190 including a pressure lumen 192 and an evacuation lumen 194.

In the illustrated embodiment, surgical instrument 182 further includes a sheath 196, which at least partially surrounds pressure lumen 192 and evacuation lumen 194 and supplies support for the lumen to assist in maintaining a geometric configuration between pressure lumen 192 and evacuation lumen 194 when the instrument 182 is in operation. Pressure lumen 192 further includes at its distal end a nozzle 198, which forms a liquid jet as a high pressure liquid supplied by pressure lumen 192 streams therethrough. Evacuation lumen 194 includes a jet-receiving opening 200 located at its distal end and positioned, when the instrument 182 is in operation, opposite the jet nozzle 198 at a predetermined distance therefrom in order to receive a liquid jet.

In some embodiments, pressure lumen 192 and evacuation lumen 194 are constructed and supported so that the distal ends of the lumens are sufficiently stiff to prevent deflection of the lumens by, for example, contact with surfaces within the surgical operating space, which deflection could potentially lead to misdirection of liquid jet so that it is no longer incident upon jet-receiving opening 200, thus potentially causing unintended tissue damage to the patient. Pressure lumen 192 is in fluid communication with high pressure pump 204 via high pressure liquid supply conduit 206. High pressure liquid supply conduit 206 must also have a burst strength capable of withstanding the highest liquid pressures contemplated for using the instrument 182 for a particular surgical application. In some embodiments, high pressure liquid supply conduit 206 comprises a burst-resistant stainless steel hypotube constructed to withstand at least 50,000 psig. In some embodiments, the hypotube may be helically coiled to improve the flexibility and maneuverability of the surgical instrument 182. In one embodiment, high pressure liquid supply conduit 206 comprises a Kevlar reinforced nylon tube that is connectable to the pressure lumen 192.

In fluid communication with high pressure liquid supply conduit 206 is the high pressure pump 204, which can be any suitable pump capable of supplying the liquid pressures required for performing the desired surgical procedure. Those of ordinary skill in the art will readily appreciate that many types of high pressure pumps may be utilized for the present purpose, including, but not limited to, piston pumps and diaphragm pumps. In some embodiments, high pressure pump 204 comprises a disposable piston or diaphragm pump, which is coupled to a reusable pump drive console 210. High pressure pump 204 has an inlet that is in fluid communication with a low pressure liquid supply line 212, which receives liquid from liquid supply reservoir 214. Pump drive console 210 preferably includes an electric motor that can be utilized to provide a driving force to high pressure pump 204 for supplying a high pressure liquid in liquid supply conduit 206. Various other details of the liquid jet surgical system 180 are described in U.S. Pat. No. 7,122,017, the details of which are incorporated by reference as if fully set forth herein.

An ultrasonic system 220 is located to impart ultrasonic energy to certain features of the liquid jet surgical system 180. Ultrasonic system 220 includes an ultrasonic signal generator 222 with ultrasonic transducer 224. The ultrasonic transducer 224 converts an electrical signal from the ultrasonic signal generator 222 into mechanical energy that results in primarily vibratory motion of the ultrasonic transducer. The transducer 224 can be designed to vibrate the system longitudinally, transversely or torsionally. In one embodiment, the transducer is a radial mode transducer located around the pressure lumen 192, for example, to impart pressure pulses to the pressurized flow.

Figure 20:
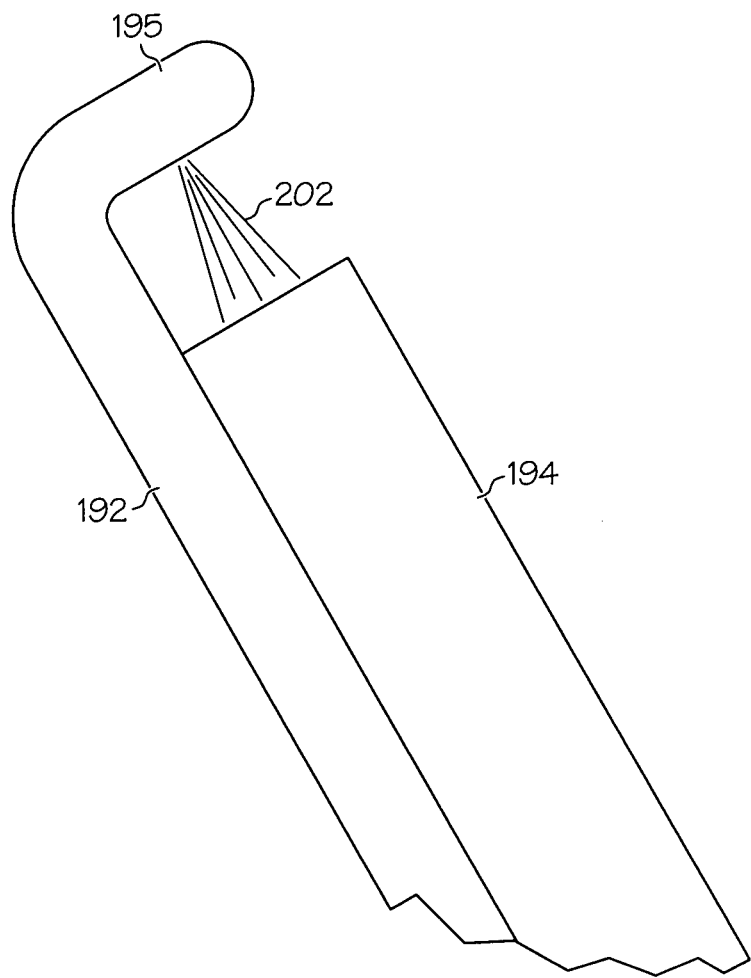
FIG. 20 is a detail view of a distal end of the ultrasonic surgical instrument of FIG. 19.

Referring now to FIG. 20, the ultrasonic transducer 224 (FIG. 19) may impart vibratory energy to any one or more of the pressure lumen 192, the evacuation lumen 194, the high pressure liquid jet 202 and the evacuation tube water column within the evacuation lumen. First, ultrasonic energy may be imparted to the pressure lumen 192. This may be accomplished by, for example, vibrating the pressure lumen 192 in a longitudinal manner thereby creating an contracting and expanding motion of the pressure lumen due to the standing wave. The dynamic motion of the tip 195 creates pressure pulses. As another example, the transducer 224 may surround the pressure lumen 102 or form part of the pressure lumen and be excited in a radial mode. This excitement causes the transducer 224 to contract the diameter of the pressure lumen 102 (which is flexible) or the fluid if the transducer is part of the lumen, thereby creating pressure pulses. By imparting ultrasonic energy to the pressure lumen 192, liquid jet cutting may be enhanced. In some instances, the pressure lumen 192 may itself be used to cut or coagulate tissue.

In some embodiments, ultrasonic energy may be imparted to the evacuation lumen 194, e.g., in a manner similar to that described above. By imparting ultrasonic energy to the evacuation lumen 194, clogging may be inhibited within the evacuation lumen 194. In some instances, the evacuation lumen 194 may itself be used to cut or coagulate tissue.

In some embodiments, ultrasonic energy may be added to the high pressure water jet 202. This may be accomplished by vibrating the pressure lumen 192 in a longitudinal manner thereby creating an contracting and expanding motion of the pressure lumen due to the standing wave. The dynamic motion of the tip 195 creates pressure pulses which impart vibratory motion to the water stream 202. As another example, the transducer 224 may surround the pressure lumen 102 or form part of the pressure lumen and be excited in a radial mode. This excitement causes the transducer 224 to contract the diameter of the pressure lumen 102 (which is flexible) or the fluid if the transducer is part of the lumen, thereby creating pressure pulses which are transferred to the water stream 202. In some embodiments, ultrasonic energy may be added to the liquid column within the evacuation lumen 194 in a manner similar to that described above.

A number of detailed embodiments have been described. Nevertheless, it will be understood that various modifications may be made. Accordingly, other embodiments are within the scope of the following claims.

What is claimed is:

1. An ultrasonic surgical system comprising:
   an ultrasonic transmission member;
   an ultrasonically actuated end-effector attached to the transmission member; and
   a sheath that is elastically moveable relative to the end-effector, the sheath having a first configuration in which a distal end of the sheath covers the end-effector to inhibit interaction with tissue by the end-effector and a second configuration in which the end-effector is exposed outside the distal end of the sheath to interact with tissue;
   wherein the sheath is moved from the first configuration to the second configuration by application of a force to the distal, terminal end of the sheath;
   wherein the sheath is configured to elastically move from the first configuration to the second configuration upon contact with hard tissue and the sheath is configured to prevent elastic movement into the second configuration upon contact with soft tissue; and
   wherein the sheath elastically returns from the second configuration to the first configuration upon removal from contact with the hard tissue.

2. The ultrasonic surgical system of claim 1 further comprising an elastic biasing member operatively connected to the sheath such that the sheath is biased toward the first configuration.

3. The ultrasonic surgical system of claim 2 further comprising:
   a connector member fixedly connected to the transmission member, the connector member including an axial portion and a radial portion extending outwardly from the axial portion, the elastic biasing member being located between the connector member and the sheath to bias the sheath toward the first configuration.

4. The ultrasonic surgical system of claim 3, wherein the elastic biasing member is a spring.

5. The ultrasonic surgical system of claim 1 further comprising a fluid delivery system, a distal end of the sheath defining a fluid nozzle for delivering pressurized fluid to tissue during use.

6. The ultrasonic surgical system of claim 1, wherein the end-effector is a composite end-effector comprising
a first portion comprising a first material having a first thermal conductivity; and
a second portion comprising a second material having a second thermal conductivity that is higher than the first thermal conductivity.

7. The ultrasonic surgical system of claim 3:
wherein the sheath includes a proximal portion that is located proximally of the connector member and a slot, formed on an inner surface of the sheath, disposed between the distal end and the proximal portion; and
wherein the slot surrounds the connector member and extends axially to permit axial movement of the sheath relative to the connector member.

8. The ultrasonic surgical system of claim 7, wherein the elastic biasing member is disposed between a distal end of the slot and the radial portion of the connector member.

9. The ultrasonic surgical system of claim 8, wherein the radial portion of the connector member engages a proximal end of the slot to limit distal movement of the sheath relative to the end-effector.

10. The ultrasonic surgical system of claim 1, wherein the distal end of the sheath includes a longitudinally extending slot configured to permit the end-effector to pass therethrough.

11. The ultrasonic surgical system of claim 10 further comprising a connector member fixedly connected to the transmission member, wherein the sheath is rotatably connected to the connector member at a pivot.

12. An ultrasonic surgical system comprising:
an ultrasonic transmission member;
an ultrasonically actuated end-effector attached to the transmission member;
a sheath that is moveable relative to the end-effector, the sheath having a first configuration in which a distal end of the sheath covers the end-effector to inhibit interaction with tissue by the end-effector and a second configuration in which the end-effector is exposed outside the distal end of the sheath to interact with tissue, and the sheath is moved from the first configuration to the second configuration by application of a force to the distal, terminal end of the sheath; and
a biasing member operatively connected to the sheath such that the sheath is biased toward the first configuration, wherein the biasing member is a spring;
wherein the sheath is configured to move from the first configuration to the second configuration upon contact with hard tissue and the sheath is configured to prevent movement into the second configuration upon contact with soft tissue.

13. The ultrasonic surgical system of claim 12 further comprising:
a connector member fixedly connected to the transmission member, the connector member including an axial portion and a radial portion extending outwardly from the axial portion, spring being located between the connector member and the sheath to bias the sheath toward the first configuration.

14. The ultrasonic surgical system of claim 12 further comprising a fluid delivery system, a distal end of the sheath defining a fluid nozzle for delivering pressurized fluid to tissue during use.

15. The ultrasonic surgical system of claim 12, wherein the end-effector is a composite end-effector comprising
a first portion comprising a first material having a first thermal conductivity; and
a second portion comprising a second material having a second thermal conductivity that is higher than the first thermal conductivity.

16. The ultrasonic surgical system of claim 13:
wherein the sheath includes a proximal portion that is located proximally of the connector member and a slot, formed on an inner surface of the sheath, disposed between the distal end and the proximal portion; and
wherein the slot surrounds the connector member and extends axially to permit axial movement of the sheath relative to the connector member.

17. The ultrasonic surgical system of claim 16, wherein the spring is disposed between a distal end of the slot and the radial portion of the connector member.

18. The ultrasonic surgical system of claim 17, wherein the radial portion of the connector member engages a proximal end of the slot to limit distal movement of the sheath relative to the end-effector.

19. The ultrasonic surgical system of claim 12, wherein the distal end of the sheath includes a longitudinally extending slot configured to permit the end-effector to pass therethrough.

20. The ultrasonic surgical system of claim 19 further comprising a connector member fixedly connected to the transmission member, wherein the sheath is rotatably connected to the connector member at a pivot.

* * * * *